(12) United States Patent
Asfora et al.

(10) Patent No.: US 10,849,661 B2
(45) Date of Patent: *Dec. 1, 2020

(54) INTERSPINOUS PROCESS DEVICE AND METHOD

(71) Applicant: ASFORA IP, LLC, Sioux Falls, SD (US)

(72) Inventors: Wilson Theophilo Asfora, Sioux Falls, SD (US); Daniel S. Savage, Brecksville, OH (US); Adam C. Sclafani, Uniontown, OH (US)

(73) Assignee: Asfora IP, LLC, Sioux Falls, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,609

(22) Filed: Sep. 18, 2017

(65) Prior Publication Data

US 2018/0000525 A1    Jan. 4, 2018

Related U.S. Application Data

(63) Continuation of application No. 14/804,950, filed on Jul. 21, 2015, now Pat. No. 9,763,707.

(51) Int. Cl.
 *A61B 17/70* (2006.01)

(52) U.S. Cl.
 CPC ............................... *A61B 17/7068* (2013.01)

(58) Field of Classification Search
 CPC ................................................. A61B 17/7068
 USPC ................................................. 606/246–249
 See application file for complete search history.

(56) References Cited

U.S. PATENT DOCUMENTS

| | | | |
|---|---|---|---|
| 1,650,772 A * | 11/1927 | Shipley | B61G 9/22 213/69 |
| 2,006,813 A * | 7/1935 | Powers | F16B 13/02 29/521 |
| 2,047,219 A * | 7/1936 | Meyer | G05G 1/12 188/74 |
| 5,723,013 A | 3/1998 | Jeanson et al. | |
| 5,947,668 A * | 9/1999 | Thommes | F16B 39/28 411/304 |
| 6,695,842 B2 | 2/2004 | Zucherman et al. | |
| 8,357,181 B2 | 1/2013 | Lange et al. | |
| 2004/0181282 A1 | 9/2004 | Zucherman et al. | |
| 2006/0282079 A1 | 12/2006 | Labrom et al. | |
| 2008/0161856 A1 | 7/2008 | Liu et al. | |
| 2008/0183211 A1* | 7/2008 | Lamborne | A61B 17/7068 606/249 |
| 2010/0036419 A1 | 2/2010 | Patel et al. | |
| 2010/0241167 A1 | 9/2010 | Taber et al. | |
| 2013/0158604 A1* | 6/2013 | Okamoto | A61F 2/44 606/249 |

(Continued)

*Primary Examiner* — Jan Christopher L Merene
(74) *Attorney, Agent, or Firm* — Fox Rothschild LLP

(57) ABSTRACT

A device for placement between two adjacent spinous processes of a spinal column to treat a spinal condition, and a method for performing a procedure on a spine of a patient, are provided. The device may include a first member, a second member mounted onto the first member, and a locking plug configured to restrict movement of the second member relative to the first member. The method may include positioning a portion of a first member between two adjacent spinous processes of the spine, advancing a second member along a length of the first member, and restricting the second member from moving relative to the first member.

21 Claims, 17 Drawing Sheets

(56) References Cited

U.S. PATENT DOCUMENTS

| | | |
|---|---|---|
| 2013/0184753 A1 | 7/2013 | Keiper et al. |
| 2013/0190820 A1* | 7/2013 | Siegfried ............ A61B 17/7068 606/248 |
| 2013/0253585 A1 | 9/2013 | Garcia et al. |
| 2013/0296940 A1* | 11/2013 | Northcutt ............ A61B 17/7008 606/249 |

* cited by examiner

INTERSPINOUS PROCESS DEVICE AND METHOD

CROSS-REFERENCE TO RELATED APPLICATIONS

The present application is related to U.S. patent application Ser. No. 14/804,950, filed Jul. 21, 2015, now U.S. Pat. No. 9,763,707, entitled "Interspinous Process Device and Method," which is incorporated herein by reference in its entirety.

FIELD

The present application relates to medical devices. More specifically, the application relates to a device for placement between adjacent spinous processes and systems and methods for implanting the device.

BACKGROUND

The spinal column is a structure principally composed of vertebrae and intervertebral disks, along with ligaments and muscles, with primary functions of supporting the body and protecting the spinal cord and associated nerve roots. The spinal column's body support functionality involves distribution of weight from the various extremities and the torso to the pelvis and legs. As individuals age, various adverse spinal column conditions may develop that often result in back pain. Examples of such conditions include spinal stenosis, thickening of spinal column constituent bones, facet antropathy, facet joint arthritis, facet synovial cyst, annular tear, painful disc disruption, and segmental instability. A number of these (and other) spinal conditions involve compression of the spinal cord or one or more nerve roots emanating from the spinal cord.

A number of efforts to address such spinal column conditions have attempted to address nerve compression issues by spreading adjacent vertebrae farther apart or at least maintaining a space between them during movement (i.e., stabilization), in order to "decompress" the impinged nervous tissue. One general type of device developed for this purpose has been interspinous implants for implantation between adjacent spinous processes. Examples of such devises are described in U.S. Pat. No. 6,695,842, U.S. Patent Application Pub. No. 2004/0181282, and others.

Although advances have been made in the treatment of spinal conditions and in interspinous implants more specifically, improvements would still be desirable. For example, several challenges with interspinous implants thus far have been that they can be difficult to implant, they can become dislodged over time due to patient movement, they can be difficult to remove if necessary, and they can damage the spinous processes adjacent to where they are implanted. The embodiments described in this application seek to address at least some of these shortcomings.

BRIEF SUMMARY

In some embodiments, a device for placement between two adjacent spinous processes of a spinal column to treat a spinal condition is provided. The device includes a first member having a post including a resilient element that is radially displaceable, and a rim disposed at or near a first end of the post and extending around a periphery of the post. The resilient element includes an outwardly protruding latching feature. The device also includes a second member mounted onto the post of the first member and movable along a length of the post to adjust a distance between the second member and the rim. The second member includes an inwardly protruding latching feature that cooperates with the outwardly protruding latching feature of the resilient element to restrict axial movement of the second member away from the rim.

In some embodiments, a device for placement between two adjacent spinous processes of a spinal column to treat a spinal condition is provided. The device includes a first member having a post including a resilient element that is displaceable transversely to a longitudinal axis of the post and a rim disposed at a first end of the post and extending around a periphery of the post. The device also includes a second member mounted onto the post of the first member. The device further includes a locking plug inserted at least partially into a second end of the post. The locking plug is configured to displace the resilient element outwardly away from the longitudinal axis of the post to restrict movement of the second member along a length of the post.

In some embodiments, a method for performing a procedure on a spine of a patient is provided. The method includes: positioning a post of a first member of an interspinous device between two adjacent spinous processes of the spine; positioning a rim of the first member on a first side of the adjacent spinous processes; positioning a second member on a second side of the adjacent spinous processes opposite the first side; advancing the second member along a length of the post of the first member toward the rim, wherein advancing the second member automatically restricts the second member from sliding along the length of the post away from the adjacent spinous processes; and moving a locking plug disposed in an end of the post relative to the post to lock the second member to the post.

These and other aspects and embodiments will be described in further detail below, in reference to the attached drawing figures. This summary of the disclosure is given to aid understanding, and each of the various aspects and features of the disclosure may advantageously be used separately in some instances, or in combination with other aspects and features of the disclosure in other instances. Accordingly, while the disclosure is presented in terms of embodiments, individual aspects of any embodiment can be claimed separately or in combination with aspects and features of that embodiment or any other embodiment. The present disclosure is set forth in various levels of detail in this application and no limitation as to the scope of the claimed subject matter is intended by either the inclusion or non-inclusion of elements, components, or the like in this summary.

BRIEF DESCRIPTION OF DRAWINGS

The accompanying drawings, which are incorporated into and constitute a part of the specification, illustrate embodiments of the disclosure and, together with the general description given above and the detailed description given below, serve to explain the principles of these embodiments.

DETAILED DESCRIPTION

Figure 1:
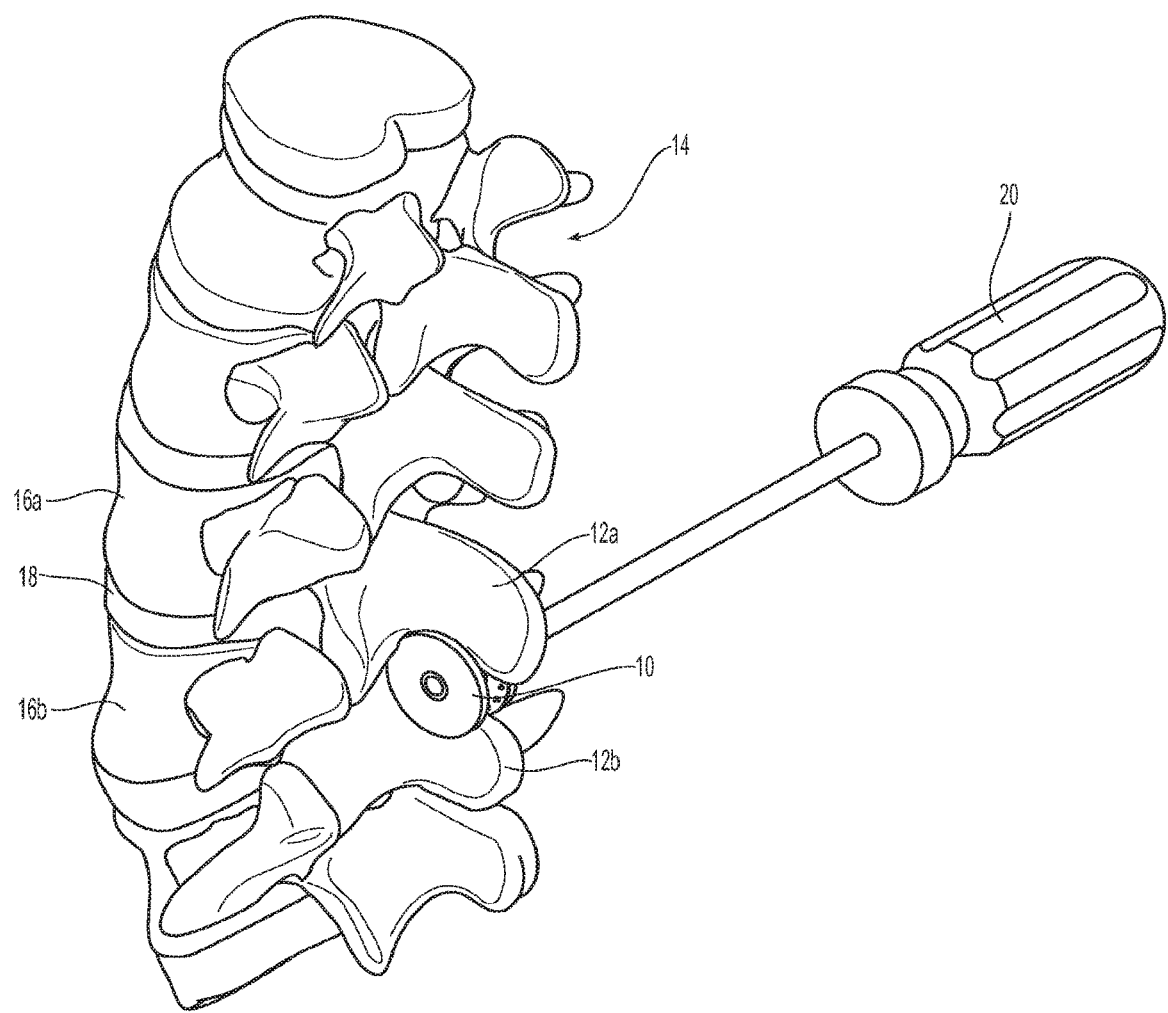
FIG. 1 is a posterior view of a device placed between two adjacent spinous processes of a spinal column and a tool for tightening or loosening the device in accordance with some embodiments of the present application.
Figure 5A:
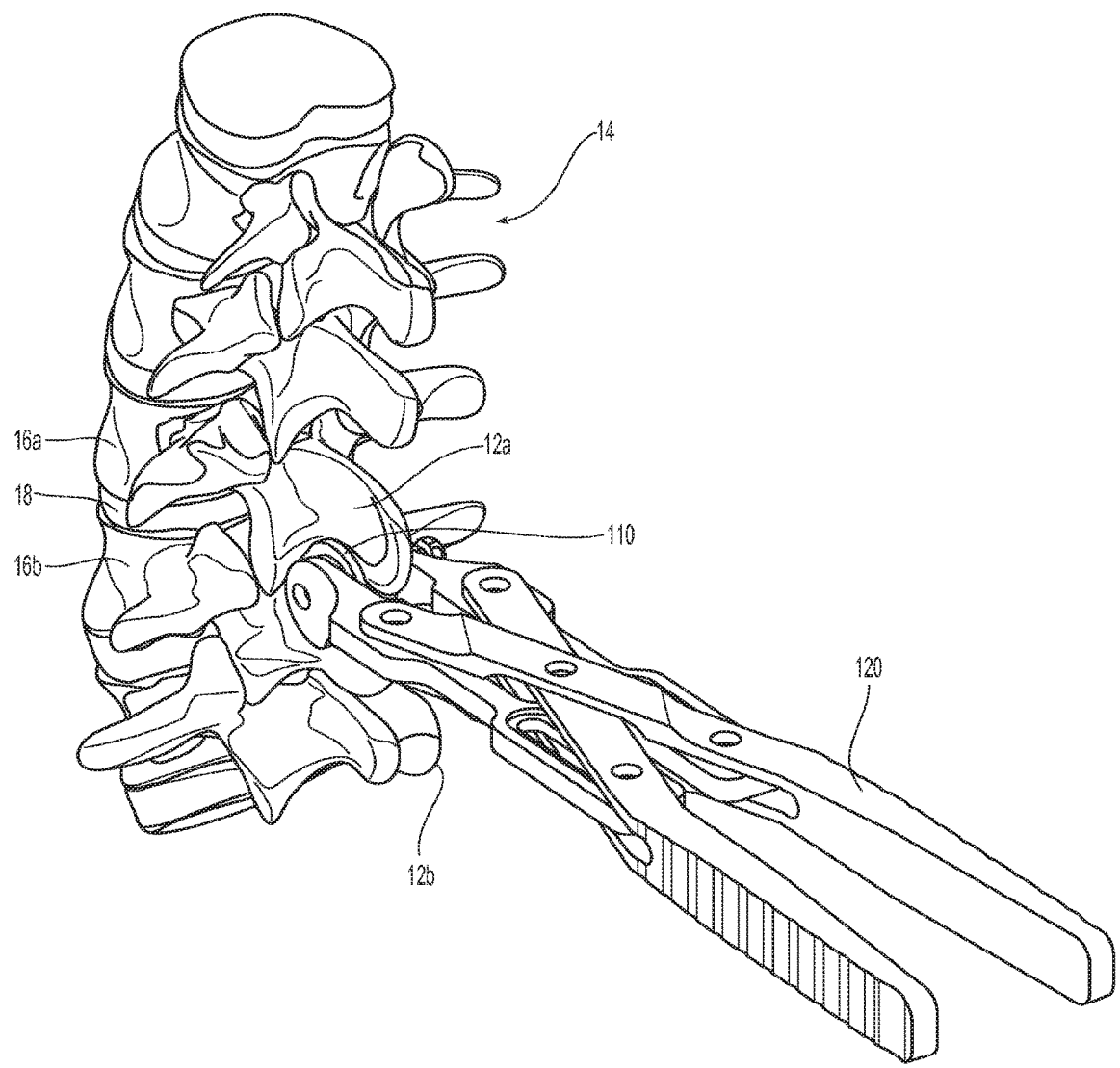
FIG. 5A is a posterior view of a device placed between two adjacent spinous processes of a spinal column and a tool for tightening the device in accordance with some embodiments of the present application.
Figure 5B:
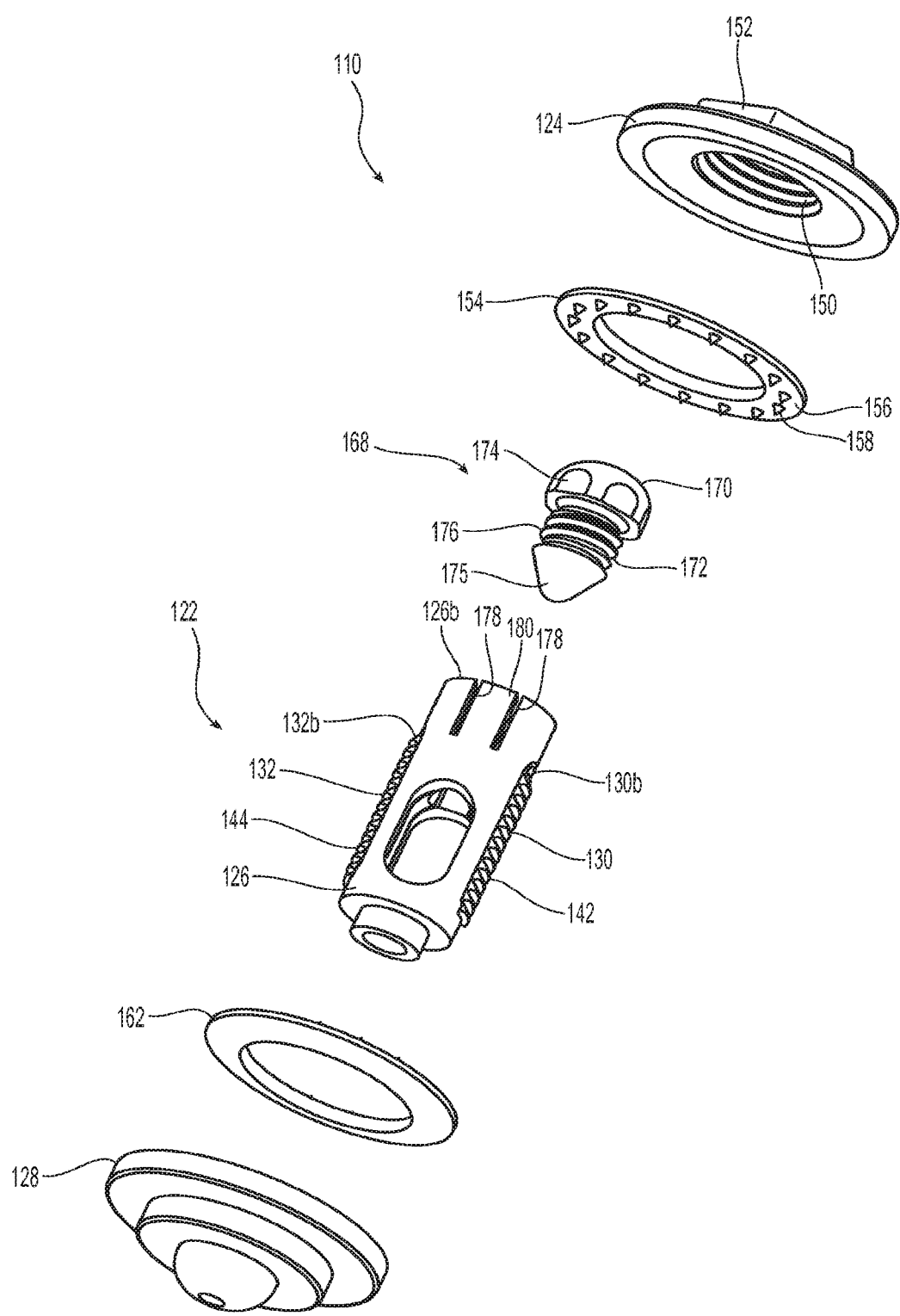
FIG. 5B is an exploded view of a device for placement between two adjacent spinous processes of a spinal column in accordance with some embodiments of the present application.
Figure 6:
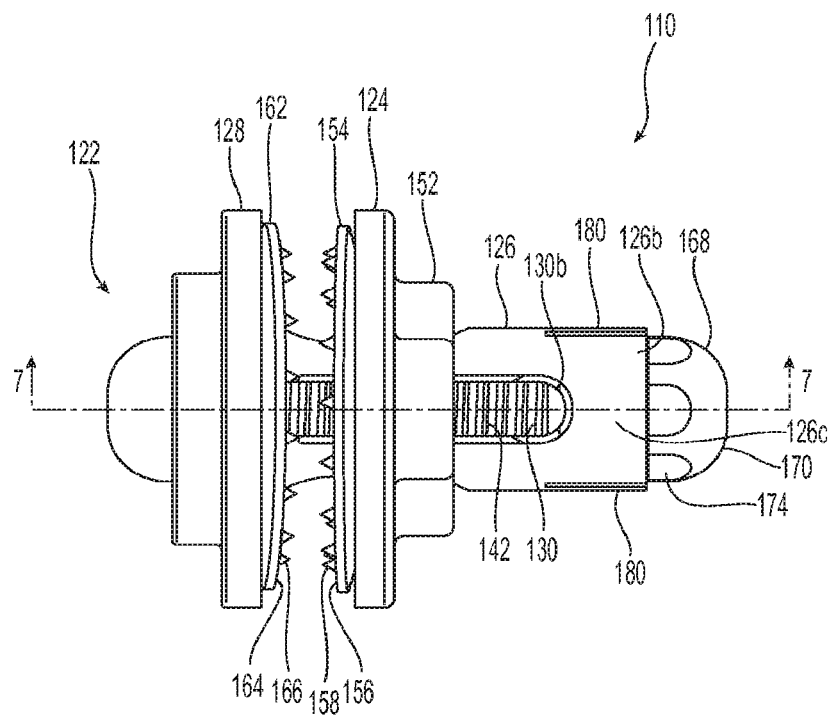
FIG. 6 is a top plan view of the device of FIG. 5 in accordance with some embodiments of the present application.

FIG. 1 is a posterior view of an illustrative embodiment of a device 10 placed between two adjacent spinous processes 12a, 12b of a spinal column 14 to treat a spinal condition. The device 10 may be coupled to the adjacent spinous processes 12a, 12b to maintain a desired spacing between the spinous processes 12a, 12b. In some applications, the device 10 substantially stabilizes the spinous processes 12a, 12b and the associated vertebrae 16a, 16b, relative to each other, to maintain a desired spacing between the associated vertebrae 16a, 16b for an intervertebral disk 18 positioned between the vertebrae 16a, 16b. A tool 20, such as the illustrated nut driver, a wrench, or other suitable tool, may be used to tighten or loosen the device 10 relative to the spinous processes 12a, 12b. In some embodiments, a compressor (see, e.g., FIG. 5A) is used to clamp the device 10 onto the spinous processes 12a, 12b, and a nut driver, wrench, or other suitable tool is used for fine tune tightening and/or removal of the device 10. The device 10 may be referred to herein as an interspinous device, indicating that a portion of the device 10 is positioned between two adjacent spinous processes 12a, 12b.

Figure 2:
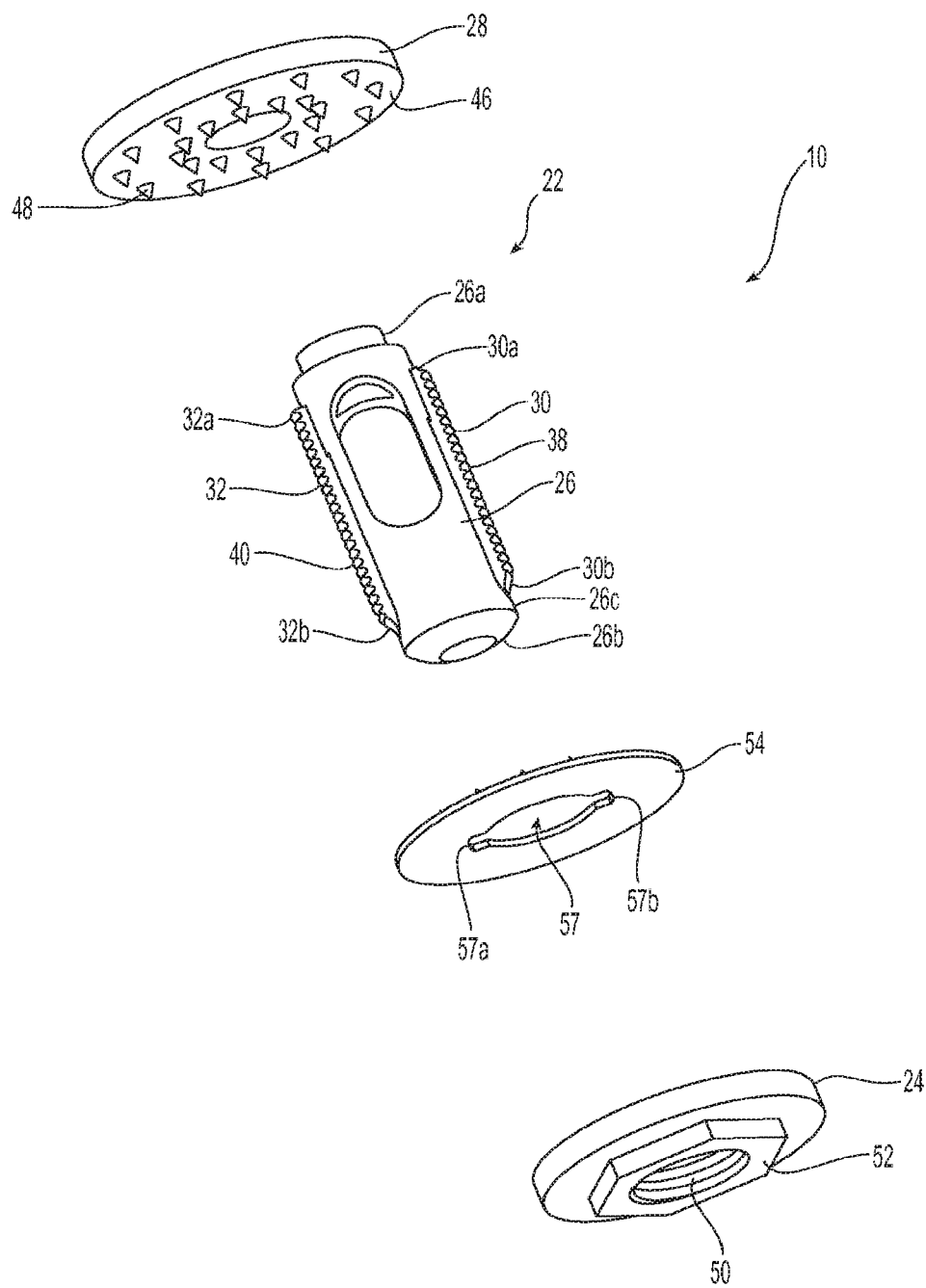
FIG. 2 is an exploded view of a device for placement between two adjacent spinous processes of a spinal column in accordance with some embodiments of the present application.
Figure 3:
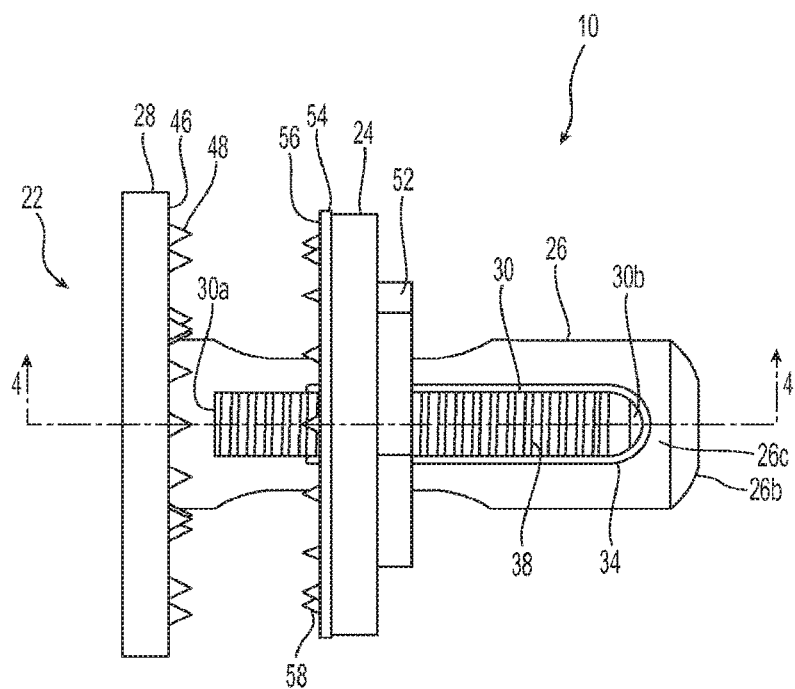
FIG. 3 is a top plan view of the device of FIG. 2 in accordance with some embodiments of the present application.
Figure 4:
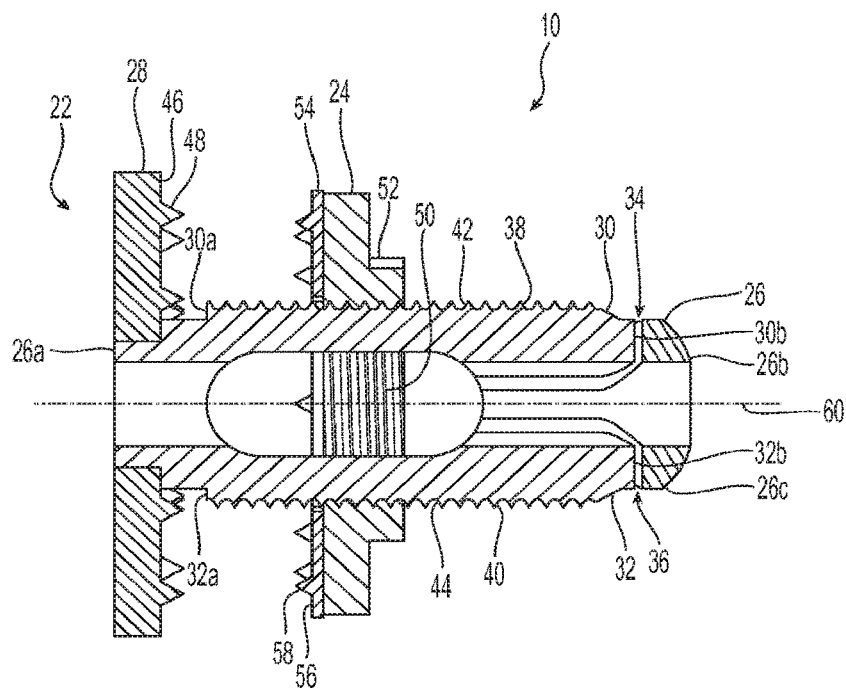
FIG. 4 is a longitudinal cross-section of the device of FIG. 2 taken along line 4-4 of FIG. 3 in accordance with some embodiments of the present application.

Referring to FIGS. 2-4, an illustrative embodiment of the device 10 is shown. The device 10 includes a first member 22 and a second member 24. The first member 22 of the illustrated embodiment includes a post 26 and a rim 28. The second member 24 of the illustrated embodiment is mounted onto the post 26 of the first member 22 and is movable along a length of the post 26 to adjust a distance between the second member 24 and the rim 28.

With continued reference to FIGS. 2-4, the post 26 may include one or more resilient elements extending lengthwise along a length of the post 26. In FIGS. 2-4, the illustrated post 26 includes a first resilient element 30 and a second resilient element 32, although the post 26 may include more or less than two resilient elements. The illustrated first and second resilient elements 30, 32 are formed on opposite sides of the post 26 and diametrically oppose each other. The illustrated first and second resilient elements 30, 32 are elongate and extend lengthwise along a length of the post 26. The first and second resilient elements 30, 32 of the illustrated embodiment include fixed ends 30a, 32a and free ends 30b, 32b, respectively. The fixed ends 30a, 32a are disposed near a first end 26a of the post 26, adjacent the rim 28, and the free ends 30b, 32b are disposed near a second end 26b of the post 26. The free ends 30b, 32b of the resilient elements 30, 32, respectively, may be spaced from the second end 26b of the post 26 by a portion 26c of the post 26 disposed between the free ends 30b, 32b of the resilient elements 30, 32 and the second end 26b of the post 26. The resilient elements 30, 32 may be defined by U-shaped slits 34, 36, respectively, formed in the post 26.

Referring still to FIGS. 2-4, the illustrated resilient elements 30, 32 include outwardly protruding latching features 38, 40, respectively. As shown in FIG. 4, the latching features 38, 40 may be formed as multiple teeth 42, 44 spaced apart from one another along a length of the resilient elements 30, 32, respectively. The teeth 42, 44 may extend transversely to a length direction of the resilient elements 30, 32, respectively, and may be parallel to one another. Collectively, the teeth 42, 44 may form a discontinuous thread that facilitates threading of the second member 24 onto the post 26 towards the rim 28 and unthreading of the second member 24 away from the rim 28 and towards the second end 26b of the post 26.

Referring to FIGS. 3 and 4, the illustrated rim 28 is disposed at or near a first end 26a of the post 26 and extends around a periphery of the post 26. The rim 28 may be referred to herein as a first spinous process interface member, such as a flange, a plate, or a washer. The rim 28 is shown as a separate component relative to the post 26; although the rim 28 and the post 26 may alternatively be formed as a single component. In the illustrated embodiment, the rim 28 is mounted onto and fixedly secured to the post 26 at or near the first end 26a of the post 26. The rim 28 may include a first medial-facing surface 46 having a lateral dimension sufficient to span between and overlap the adjacent spinous processes 12a, 12b. The first medial-facing surface 46 may face towards the second member 24 and may include a surface feature capable of being embedded in the adjacent spinous processes 12a, 12b. The surface feature may provide a secure connection between the device 10 and a portion of the spinous processes 12a, 12b placed against the surface feature to inhibit movement of the spinous processes 12a, 12b relative to the device 10. The surface feature may include protrusions, roughening, or both. For example, in FIGS. 2-4, the rim 28 includes a first set of sharp protrusions 48 on the first medial-facing surface 46. The surface feature may include, but is not limited to, spikes, teeth, scoring, sharp protrusions, ridges, serrations, or other suitable type of surface features capable of inhibiting movement of the spinous processes 12a, 12b relative to the device 10.

With reference to FIGS. 2 and 4, the second member 24 may be annular or ring-shaped, and may be referred to herein as a nut. The second member 24 may define a central bore dimensioned to receive the post 26 of the first member 24. The second member 24 may include an inwardly protruding latching feature 50 that cooperates with the outwardly protruding latching features 38, 40 of the resilient elements 30, 32, respectively, to restrict axial movement of the second member 24 away from the rim 28. The inwardly protruding latching feature 50 may be formed as an internal thread that is ratchetably and threadably engagable with the outwardly protruding latching features 38, 40 of the resilient elements 30, 32. As the second member 24 is slid along the length of the resilient elements 30, 32, the inwardly protruding latching feature 50 may interdigitate with the teeth 42, 44 in a ratcheting manner. Additionally, or alternatively, the second member 24 may be threaded onto the resilient elements 30, 32 via the latching features.

Referring to FIGS. 2-4, the second member 24 may include an engagement feature 52 protruding from a side of the second member 24 facing away from the rim 28. The engagement feature 52 may be configured for coupling with a tool, such as a nut driver or wrench. The illustrated engagement feature 52 is formed with a hexagonal periphery, although other polygonal or non-circular shapes may be used. The engagement feature 52 may facilitate embedding of the sharp protrusions 48 into the spinous processes 12a, 12b.

Referring to FIGS. 2-4, the device 10 may include a third member 54 mounted on the post 26 between the rim 28 and the second member 24. The third member 54 may be annular or ring-shaped. The third member 54 may be referred to herein as a second spinous process interface member, such as a plate or washer. The third member 54 may define a central bore 57 dimensioned to receive the post 26 and may include two keyways 57a, 57b dimensioned to permit passage of the resilient elements 30, 32 during advancement of the third member 54 along a length of the post 26. The third member 54 of the illustrated embodiment includes a first medial-facing surface 56. The first medial-facing surface 56 may face towards the first medial-facing surface 46 of the rim 28 and may include a surface feature capable of being embedded in the adjacent spinous processes 12a, 12b.

The surface feature may provide a secure connection between the device 10 and a portion of the spinous processes 12a, 12b placed against the surface feature to inhibit movement of the spinous processes 12a, 12b relative to the device 10. The surface feature may include protrusions, roughening, or both. For example, in FIGS. 3 and 4, the third member 54 includes a first set of sharp protrusions 58 on the first medial-facing surface 56. The surface feature may include, but is not limited to, spikes, teeth, scoring, sharp protrusions, ridges, serrations, or other suitable type of surface features capable of inhibiting movement of the device 10 relative to the respective spinous processes. Referring to FIG. 4, the first member 22, the second member 24, and the third member 54 may be coaxially aligned along a longitudinal axis 60 of the post 26.

To implant the device 10 in the spinal column 14 of a patient, the post 26 may be placed between two adjacent spinous processes 12a, 12b with the rim 28 positioned on a first side of the spinous processes 12a, 12b and the second member 24 positioned on a second side of the spinous processes 12a, 12b opposite the first side. The second member 24 may be advanced along a length of the post 26 toward the rim 28. For example, the second member 24 may be slid along the length of the post 26 toward the rim 28, causing the resilient elements 30, 32 to resiliently deform inwardly toward the longitudinal axis 60 of the post 26 during ratcheting of the inwardly protruding latching feature 50 of the second member 24 over the outwardly protruding latching features 38, 40 of the resilient elements 30, 32. A compressor instrument (see FIG. 5A) may be used to advance the second member 24 along the post 26. Additionally, or alternatively, the second member 24 may be threaded along the length of the post 26 toward the rim 28 for tightening or removing the second member 24 from the post 26, for example. The latching features 38, 40 of the resilient elements 30, 32 and the latching feature 50 of the second member 24 may interdigitate with one another and restrict the second member 24 from sliding along the length of the post 26 away from the rim 28, but may permit unscrewing of the second member 24 along the post 26 away from the rim 28.

To embed the sharp protrusions 48, 58 into the spinous processes 12a, 12b, a first tool (e.g., the compressor shown in FIG. 5A) may be used to clamp the spinous processes 12a, 12b between the rim 28 and the third member 54. A second tool (e.g., the nut driver shown in FIG. 1) may be used to engage the engagement feature 52 and rotate the second member 24 relative to the post 26 to move the second member 24 toward the rim 28, thereby providing fine tune adjustment of the clamping force applied to the spinous processes 12a, 12b by the rim 28 and the third member 54. To remove the device 10 from between two adjacent spinous processes 12a, 12b, the second member 24 may be unthreaded from the post 26 to move the second member 24 away from the rim 28. The sharp protrusions 48, 58 may be disengaged from the spinous processes 12a, 12b, and the third member 54 may be moved away from the rim 28 a sufficient distance to permit removal of the device 10 from the spinal column 14.

Referring to FIGS. 5A-10, another embodiment of a device 110 for placement between two adjacent spinous processes 12a, 12b of a spinal column 14 is depicted. The device 110 is similar to the device 10 shown in FIGS. 1-4. Accordingly, the preceding discussion related to the device 10 is applicable to the device 110 shown in FIGS. 5-10, except as noted below. The reference numerals used in FIGS. 5A-10 are incremented by one-hundred relative to the reference numerals used in FIGS. 1-4 to reflect similar parts.

Similar to the device 10 depicted in FIGS. 1-4, the device 110 includes a first member 122, a second member 124, and a third member 154. The first member 122 includes a post 126 and a rim 128. The second member 124 is mounted onto the post 126 of the first member 122 and is movable along a length of the post 126 to adjust a distance between the second member 124 and the rim 128. The second member 124 may be referred to herein as a nut.

Similar to the post 26 depicted in FIGS. 1-4, the post 126 illustrated in FIGS. 5A-10 includes a first resilient element 130 and a second resilient element 132, although the post 126 may include more or less than two resilient elements. The resilient elements 130, 132 may include outwardly protruding latching features 138, 140, which may be formed as a series of teeth 142, 144, respectively. The second member 124 may include an inwardly protruding latching feature 150 that cooperates with the outwardly protruding latching features 138, 140 of the resilient elements 130, 132, respectively, to restrict axial movement of the second member 124 away from the rim 128. The inwardly protruding latching feature 150 may be formed as an internal thread that is ratchetably and threadably engagable with the outwardly protruding latching features 138, 140 of the resilient elements 130, 132. As the second member 124 is slid along the length of the post 126, the second member 124 may ratchet onto the resilient elements 130, 132 such that the inwardly protruding latching feature 150 interdigitates with the teeth 142, 144 and intermittently displaces the resilient elements 130, 132 inwardly toward the longitudinal axis 160 of the post 126. A compressor 120 (see FIG. 5A) may be used to move the second member 124 along the post 126 toward the rim 128. The compressor 120 may include first and second jaws positioned on opposite sides of the spinous processes 12a, 12b. The rim 128 may be positioned between the first jaw and the adjacent spinous processes 12a, 12b, and the second member 124 may be positioned between the second jaw and the adjacent spinous processes 12a, 12b. An installer may squeeze handles connected to the first and second jaws to apply a compressive force to the jaws and move the second member 124 axially along the post 126 toward the rim 128, thereby clamping the spinous processes 12a, 12b between the rim 128 and the second member 124. Additionally, or alternatively, the installer may threadably rotate the second member 124 along the post 126 to advance the second member 124 toward the rim 128. Similar to the second member 24 depicted in FIGS. 1-4, the second member 124 may include an engagement feature 152 for coupling with a tool, such as a wrench or the nut driver shown in FIG. 1.

With continued reference to FIGS. 5A-10, the device 110 may include a third member 154 mounted onto the post 126 between the rim 128 and the second member 124, similar to the device 10 depicted in FIGS. 1-4. The third member 154 may be referred to herein as a spinous process interface member, such as a flange, a plate, or a washer. The third member 54 may define a central bore 157 dimensioned to receive the post 126. The central bore 157 may be oversized relative to the post 126 such that the central bore 157 does not need keyways for the resilient elements 130, 132 to pass through the central bore 157 during advancement of the third member 154 along a length of the post 126. The third member 154 of the illustrated embodiment includes a first medial-facing surface 156 having a surface feature, such as sharp protrusions 158, capable of being embedded in the adjacent spinous processes 12a, 12b.

With continued reference to FIGS. 5A-10, the device 110 may include a fourth member 162 mounted onto the post 126 and disposed between the rim 128 and the third member 154. The fourth member 162 may be referred to herein as a spinous process interface member, such as a flange, a plate, or a washer. The illustrated fourth member 162 includes a second medial-facing surface 164 and a surface feature, such as a second set of sharp protrusions 166, on the second medial-facing surface 164. As shown in FIGS. 6-9, the illustrated first and second medial-facing surfaces 156, 164 face each other. The first and second medial-facing surfaces 156, 164 may have lateral dimensions sufficient to span between and overlap the adjacent spinous processes 12a, 12b on opposite sides of the spinous processes 12a, 12b. The third and fourth members 154, 162 may be formed as spring washers, such as Belleville washers, to provide the third and fourth members 154, 162 with a spring characteristic during attachment of the device 110 to the adjacent spinous processes 12a, 12b. The profile of the third and fourth members 154, 162 may provide a degree of rotational freedom between the third and fourth member 154, 162 to improve the fit with the spinous process anatomy.

During connection of the device 110 to the adjacent spinous processes 12a, 12b of a spinal column 14, the rim 128 and the fourth member 162 may be positioned on one side of the spinous processes 12a, 12b, the second and third members 124, 154 may be positioned on an opposite side of the spinous processes 12a, 12b, and the post 126 may extend from the rim 128 to the second member 124 between the spinous processes 12a, 12b. The second member 124 may be ratcheted along the length of the post 126 toward the rim 128 by the compressor 120, for example, causing the third member 154 to move axially towards the fourth member 162. To finely adjust the clamping force applied to the spinous processes 12a, 12b by the third and fourth members 154, 162, the installer may use a tool 20, such as a nut driver or wrench, to engage the engagement feature 152 and move the second member 124 further towards the rim 128. The third and fourth members 154, 162 may be formed as spring washers. The third and fourth members 154, 162 may apply a pre-load to the connection between the device 110 and the spinous processes 12a, 12b.

With further reference to FIGS. 5A-10, the device 110 of the illustrated embodiment includes a locking plug 168 inserted at least partially into the second end 126b of the post 126 to restrict movement of the second member 124 away from the rim 128. The illustrated locking plug 168 includes an engagement feature 170 and a securement feature 172.

The engagement feature 170 may include multiple peripheral flat sections 174 disposed adjacent the second end 126b of the post 126 for engagement with a tool, such as a nut driver or a wrench. The securement feature 172 may include an external thread 176 and may be positioned between a cam feature 175 and the engagement feature 170 of the locking plug 168. During insertion of the locking plug 168 into the second end 126b of the post 126, the external thread 176 may threadedly engage an internally-threaded portion of the second end 126b of the post 126, and rotation of the locking plug 168 relative to the post 126 in a first rotational direction may advance the locking plug 168 towards the rim 128. The post 126 may include longitudinal slits 178 extending lengthwise along the length of the post 126 and opening through the second end 126b of the post 126. Cantilevered fingers 180 may be defined by the slits 178, and may facilitate insertion of the locking plug 168 into the central bore 182 of the post 126. Similar to the advancement of the second member 124 along the post 126, the locking plug 168 may be axially inserted into the end of the post 126, causing the cantilevered fingers 180 to resiliently flex outwardly during ratcheting of the external thread 176 of the plug 168 and the internally-threaded portion of the post 126. A compressor instrument, similar to compressor 120, may be used to axially insert or compress the locking plug 168 into the end of the post 126. The interface between the resilient fingers 180 and the plug 168 may provide sufficient rotational resistance, such as frictional resistance, to prevent unintentional unthreading of the plug 168 from the post 126. To remove the plug 168 from the post 126, the plug 168 may be unthreaded from the post 126 by a tool, such as a nut driver or wrench, to unlock the second member 124.

Figure 7:
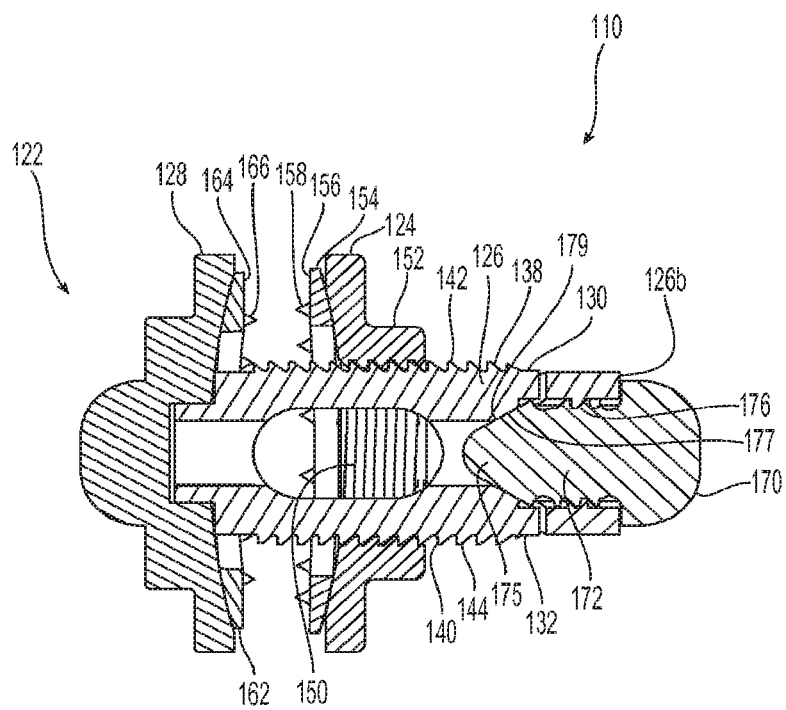
FIG. 7 is a longitudinal cross-section of the device of FIG. 5 taken along line 7-7 of FIG. 6 in accordance with some embodiments of the present application.
Figure 8:
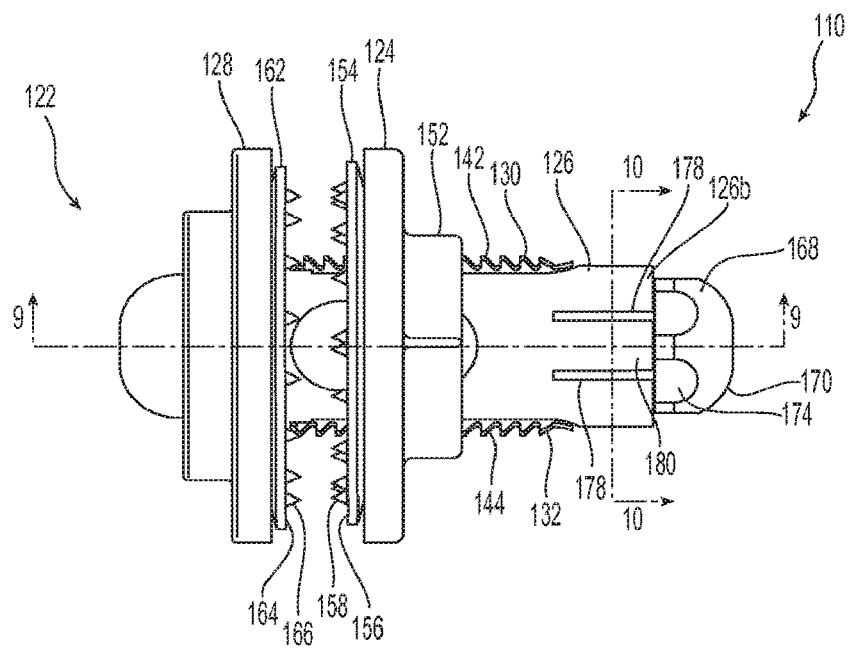
FIG. 8 is a front elevation view of the device of FIG. 5 in accordance with some embodiments of the present application.
Figure 9:
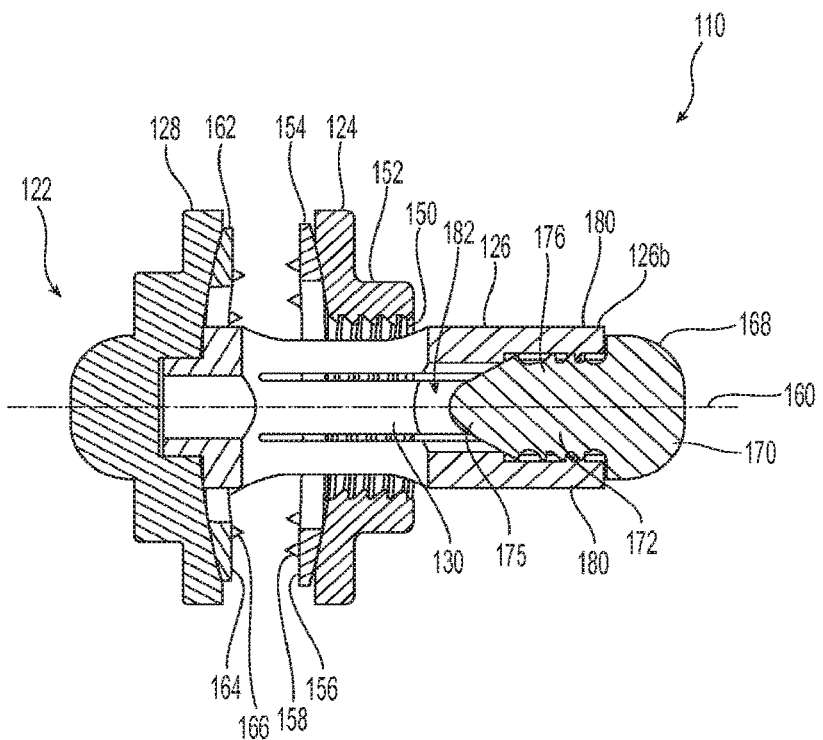
FIG. 9 is a longitudinal cross-section of the device of FIG. 5 taken along line 9-9 of FIG. 8 in accordance with some embodiments of the present application.
Figure 10:
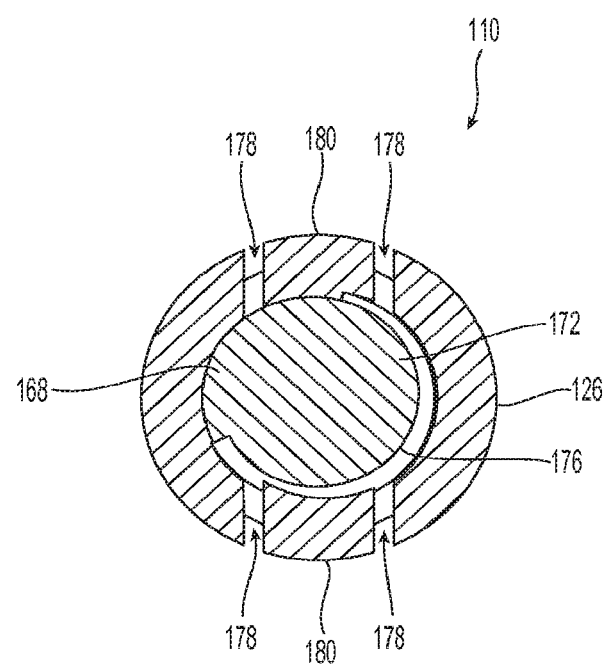
FIG. 10 is a transverse cross-section of the device of FIG. 5 taken along line 10-10 of FIG. 8 in accordance with some embodiments of the present application.
Figure 11:
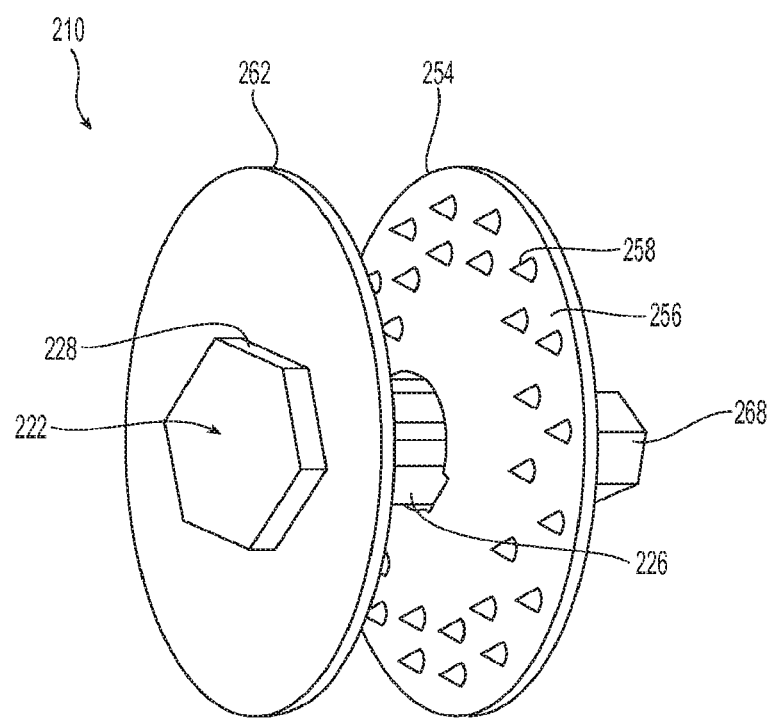
FIG. 11 is a perspective view of a device for placement between two adjacent spinous processes of a spinal column in accordance with some embodiments of the present application.
Figure 12:
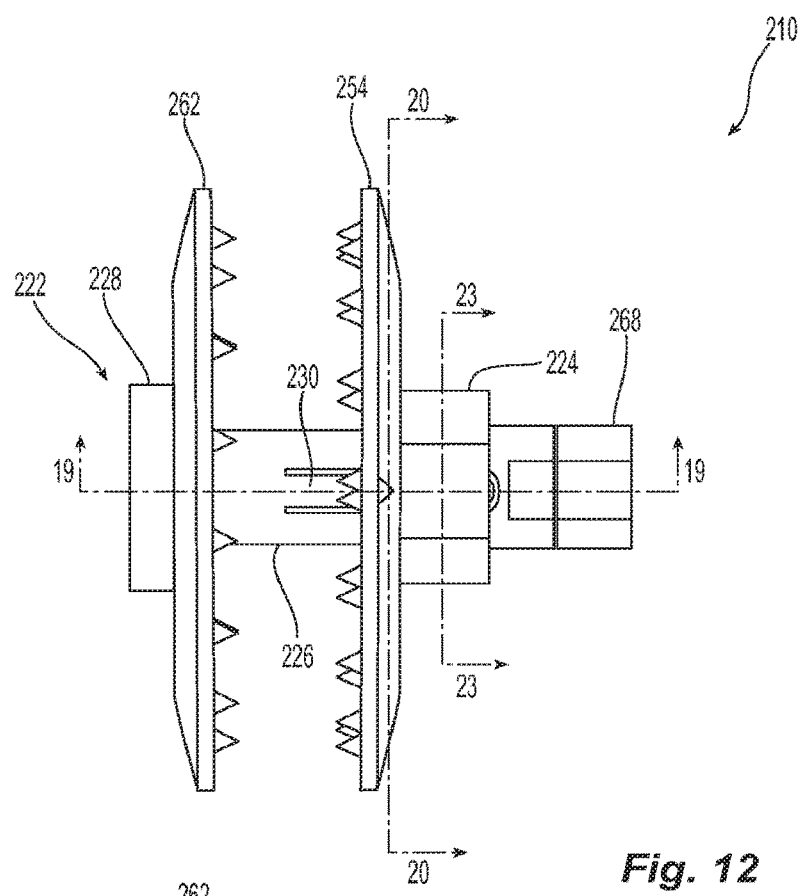
FIG. 12 is a top plan view of the device of FIG. 11 in accordance with some embodiments of the present application.
Figure 13:
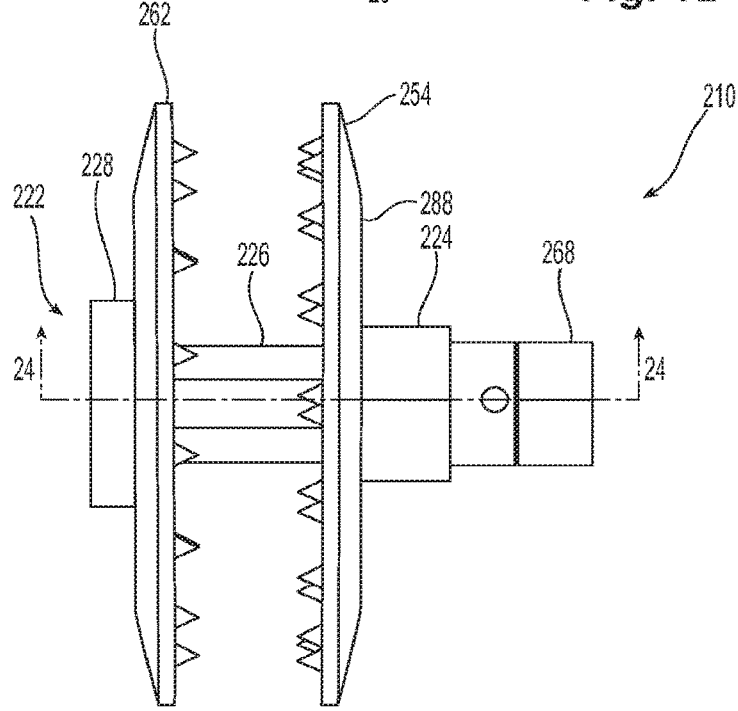
FIG. 13 is a front elevation view of the device of FIG. 11 in accordance with some embodiments of the present application.

During advancement of the locking plug 168 toward the rim 128, the cam feature 175 of the locking plug 168 engages the resilient elements 130, 132 proximate their free ends 130b, 132b. The engagement of the locking plug 168 with the resilient elements 130, 132 causes the free ends 130b, 132b of the resilient elements 130, 132 to resiliently flex outwardly away from a longitudinal axis 160 of the post 126 relative to their fixed ends 130a, 132a, thereby tightening a connection between the outwardly protruding latching features 138, 140 of the resilient elements 130, 132, and the inwardly protruding latching feature 150 of the second member 124. The tightened connection may restrict the second member 124 from moving axially away from the rim 128. As shown in FIG. 7, the cam feature 175 may include a conical or frustoconical cam surface 177 for contacting corresponding cam surfaces 179 of the resilient elements 130, 132 and radially displacing the free ends 130b, 132 of the resilient elements 130, 132 away from the longitudinal axis 160 (see FIG. 9) of the post 126. To remove the second member 124 from the first member 122, the locking plug 168 may be rotated in a second rotational direction opposite the first rotational direction to unthread the locking plug 168 from the second end 126b of the post 126 and disengage the locking plug 168 from the resilient elements 130, 132, thereby allowing the resilient elements 130, 132 to resiliently return to their original location permitting unthreading of the second member 124 from the post 126.

Referring to FIGS. 11-24, another embodiment of a device 210 for placement between two adjacent spinous processes 12a, 12b of a spinal column 14 is depicted. The device 210 is similar to the devices 10, 110 depicted in FIGS. 1-10. Accordingly, the preceding discussion related to the devices 10, 110 is applicable to the device 210 shown in FIGS. 11-24, except as noted below. The reference numerals used in FIGS. 11-24 are incremented by one-hundred relative to the reference numerals used in FIGS. 5-10 to reflect similar parts.

Figure 14:
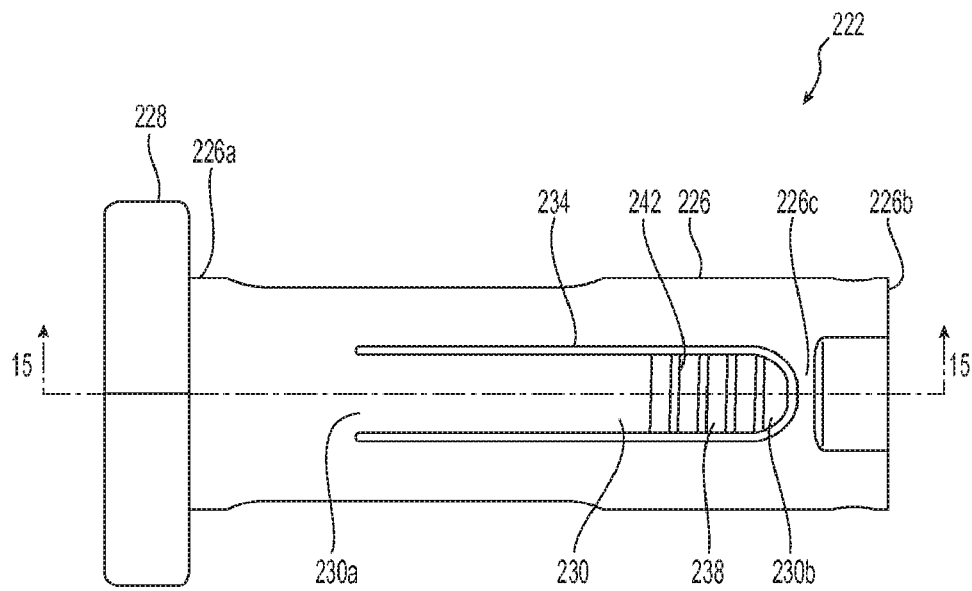
FIG. 14 is a top plan view of a first member of the device of FIG. 11 in accordance with some embodiments of the present application.
Figure 15:
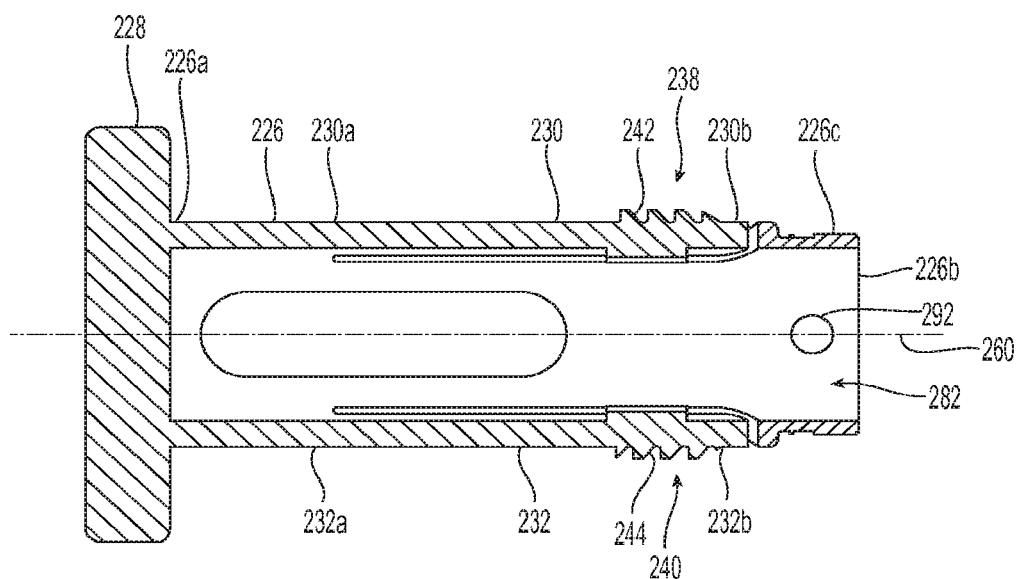
FIG. 15 is longitudinal cross-section of the first member of FIG. 14 taken along line 15-15 of FIG. 14 in accordance with some embodiments of the present application.

Similar to the device 10 depicted in FIGS. 1-4, the device 210 of the illustrated embodiment includes a first member 222, a second member 224, a third member 254, a fourth member 262, and a locking plug 268. Referring to FIGS. 14 and 15, the first member 122 includes a post 226 and a rim 228 disposed at or near a first end 226a of the post 226. The post 226 includes first and second resilient elements 230, 232 with outwardly protruding latching features 238, 240, such as ratchet teeth 242, 244, respectively. The resilient elements 230, 232 may be displaceable transversely to a longitudinal axis 260 of the post 226 (see FIG. 15). For example, the resilient elements 230, 232 may be resiliently displaced inwardly during ratcheting of the second member 224 over the latching features 238, 240 when the second member 224 is slid along the length of the post 226 toward the rim 228 during connection of the device 210 to the spinous processes 12a, 12b. The post 226 may be formed as a substantially cylindrical tube defining a central bore 282 extending from a first end 226a to a second end 226b of the post 226. The rim 228 may enclose the first end 226a of the post 226 and may be formed as a unitary part with the post 226. The rim 228 may extend outwardly from a periphery of the post 226 to define a shoulder for the fourth member 262 to abut against (see FIG. 19) when the device 210 is installed in a spinal column 14. The third and fourth members 254, 262 may have lateral dimensions sufficient to span between and overlap the adjacent spinous processes 12a, 12b on opposite sides of the spinous processes 12a, 12b. The second member 224 may be referred to herein as a nut, and the third and fourth members 254, 262 may be referred to herein as spinous process interface members, such as a flange, a plate, or a washer.

Figure 16:
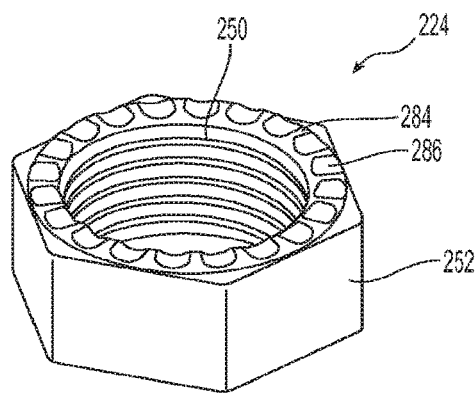
FIG. 16 is a perspective view of a second member of the device of FIG. 11 in accordance with some embodiments of the present application.

Referring to FIGS. 12, 13, 16, and 19, the second member 224 of the illustrated embodiment is mounted onto the post 126 of the first member 122 and is movable along a length of the post 126 to adjust a distance between the second member 124 and the rim 128. Referring to FIG. 16, the second member 224 may include an inwardly protruding latching feature 250, such as an internal thread, configured to cooperate with the latching features 238, 240 of the resilient elements 230, 232. During sliding of the second member 224 along the length of the post 226 toward the rim 228, the latching feature 250 of the second member 224 may ratchet over the latching features 238, 240 of the resilient elements 230, 232. Additionally, or alternatively, the second member 224 may be threaded along the first and second resilient elements 230, 232 to axially advance the second member 224 along the post 226 toward the rim 228. The second member 224 may include an engagement feature 252 to facilitate engagement with a tool, such as a nut driver or a wrench.

Figure 19:
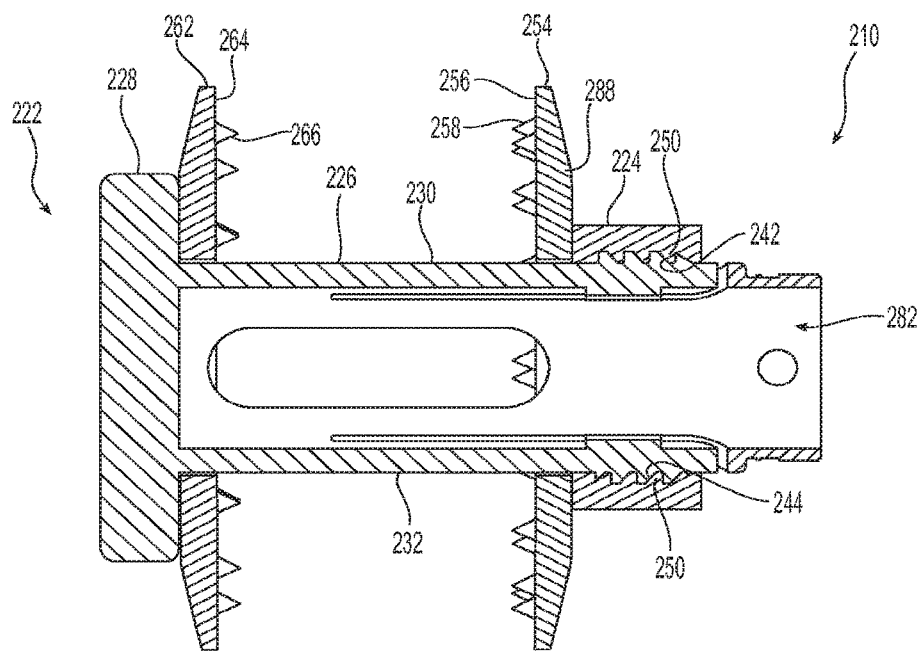
FIG. 19 is a longitudinal cross-section of the device of FIG. 11 taken along line 19-19 of FIG. 12 with a locking plug and a cross pin removed for description purposes in accordance with some embodiments of the present application.
Figure 20:
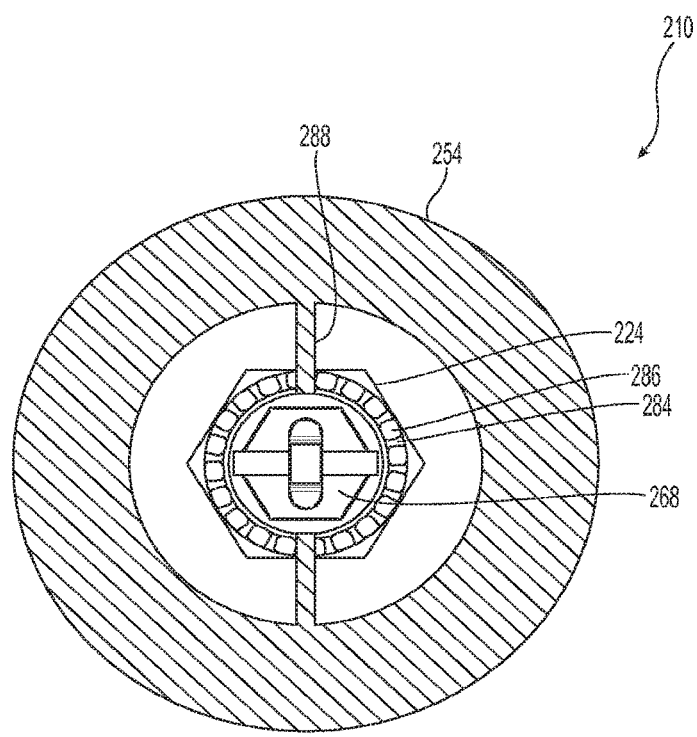
FIG. 20 is a transverse cross-section of the device of FIG. 11 taken along line 20-20 of FIG. 12 in accordance with some embodiments of the present application.

Referring to FIG. 16, the second member 224 may be castellated with alternating ribs 284 and grooves 286 disposed around an end face of the member 224. Referring to FIGS. 19 and 20, the ribs 284 and the grooves 286 may confront the third member 254. As shown in FIG. 20, the grooves 286 may receive a rib 288 protruding from a confronting surface of the third member 254 to restrict rotation of the second member 224 relative to the third member 254. The seating of the rib 288 in the grooves 286 may help secure the second member 224 in place when the device 210 is secured to the spinous processes 12a, 12b.

Figure 17:
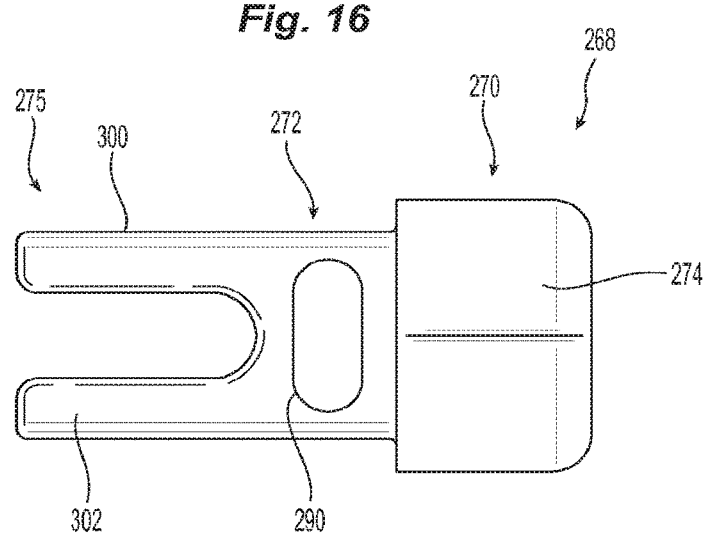
FIG. 17 is a top plan view of a locking plug of the device of FIG. 11 in accordance with some embodiments of the present application.
Figure 18:
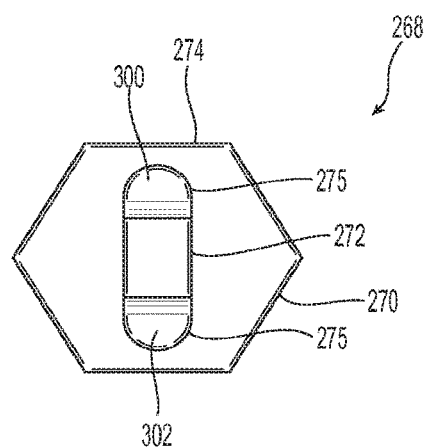
FIG. 18 is an end view of the locking plug of FIG. 17 in accordance with some embodiments of the present application.

Referring to FIGS. 17 and 18, the locking plug 268 of the illustrated embodiment may include an engagement feature 270, a cam feature 275, and a securement feature 272 located axially between the engagement feature 270 and the cam feature 275. The engagement feature 270 may include multiple peripheral flat sections 274 disposed beyond the second end 126b of the post 126 for engagement with a tool, such as a nut driver or a wrench. The securement feature 272 may define an aperture 290 extending through the securement feature 272 transverse to the longitudinal axis 260 of the post 226 (see FIG. 15). When the locking plug 268 is at least partially received in the bore 282 of the post 226, the aperture 290 of the locking plug 268 may be aligned with an apertures 292 of the post 226 (see FIGS. 15 and 21).

Figure 22:
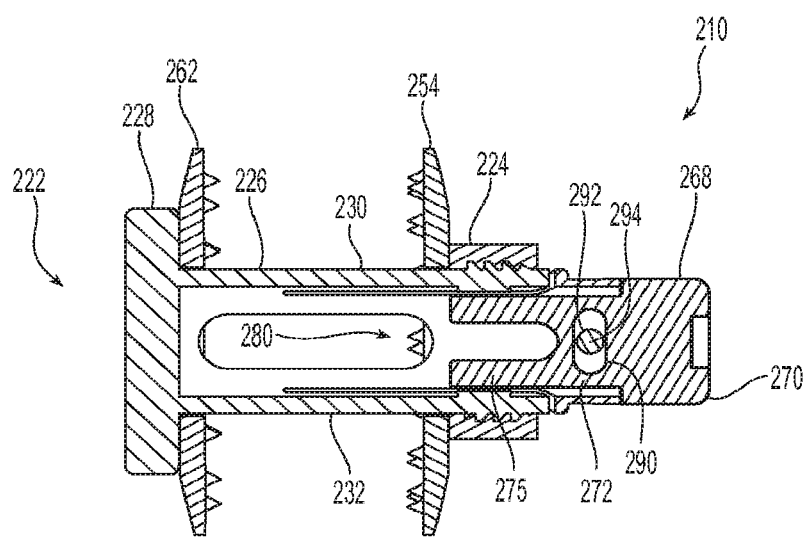
FIG. 22 is a longitudinal cross-section of the device of FIG. 11 taken along line 19-19 of FIG. 12 in accordance with some embodiments of the present application.
Figure 23:
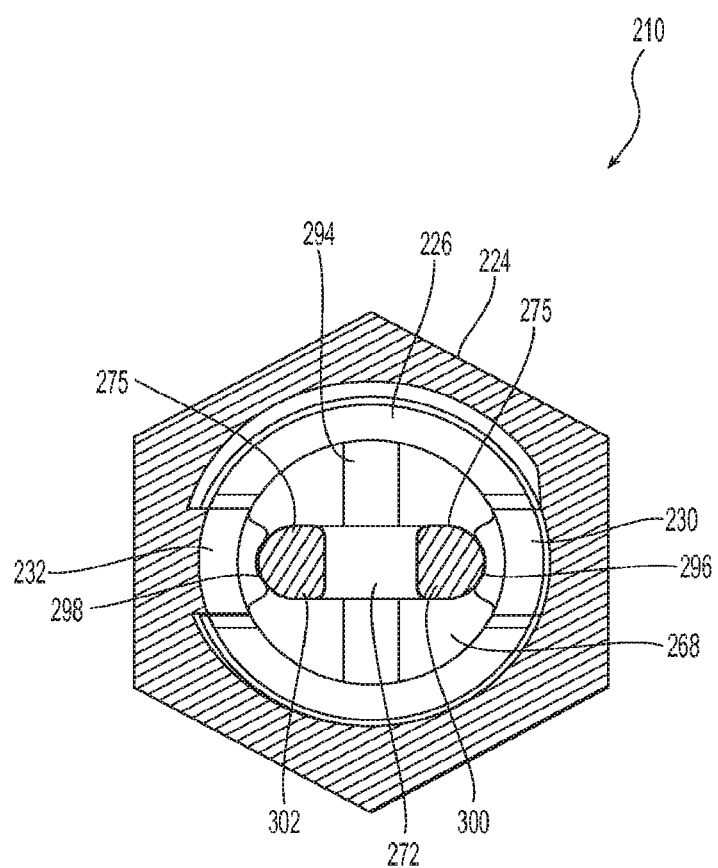
FIG. 23 is a transverse cross-section of the device of FIG. 11 taken along line 23-23 of FIG. 12 in accordance with some embodiments of the present application.
Figure 24:
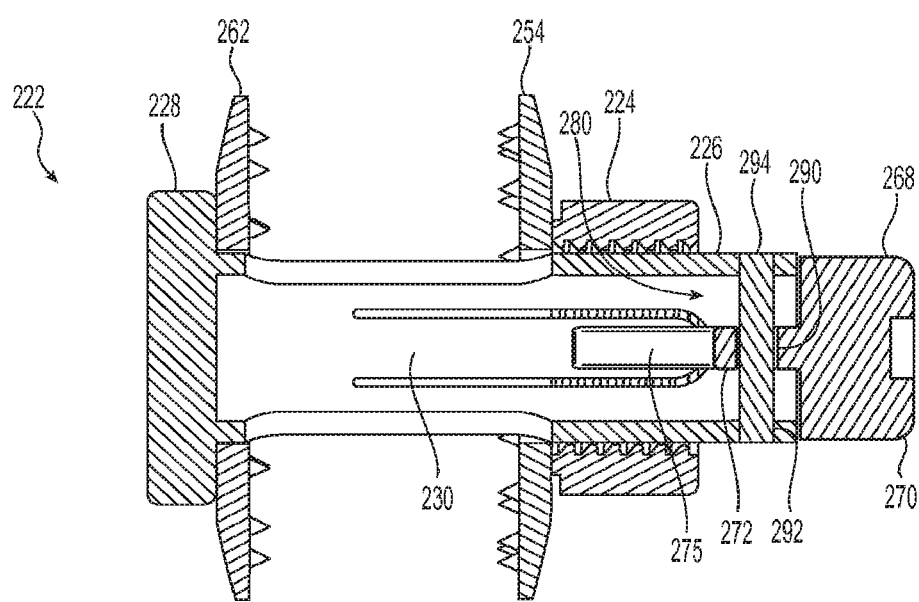
FIG. 24 is a longitudinal cross-section of the device of FIG. 11 taken along line 24-24 of FIG. 13 in accordance with some embodiments of the present application.

Referring to FIGS. 22-24, a cross pin 294 may be placed through the aperture 290 and snugly received in the apertures 292 of the post 226 to secure the locking plug 268 to the post 226. The dimensions of the cross pin 294 and the aperture 290 may be substantially the same along a length dimension of the locking plug 268 to restrict axial movement of the locking plug 268 relative to the post 226. The aperture 290 may have a larger lateral dimension relative to the cross pin 294 to permit rotation of the locking plug 268 relative to the cross pin 294, and thus the post 226.

Referring to FIGS. 21-24, the locking plug 268 of the illustrated embodiment is inserted into a bore 280 formed in a second end 226b of the post 226. The cam feature 275 of the locking plug 268 engages an inner surface of the resilient elements 230, 232 to resiliently bend or flex the free ends 230b, 232b of the resilient elements 230, 232 outwardly away from the longitudinal axis 260 of the post 226 relative to their fixed ends 230a, 232a and tighten a connection between the second member 224 and the post 226, thereby restricting axial movement of the second member 224 away from the rim 228. As shown in FIG. 23, the resilient elements 230, 232 may include cam features 296, 298 on an inner surface of the resilient elements 230, 232. The illustrated locking plug 268 is rotatable relative to the post 226 to selectively engage the cam feature 275 of the locking plug 268 with the cam features 296, 298 of the resilient elements 230, 232. When engaged, the cam feature 275 drives the free ends 230b, 232b of the resilient elements 230, 232 radially outwardly to tighten the connection between the latching features 238, 240 of the resilient elements 230, 232 and the latching feature 250 of the second member 224, thereby substantially preventing axial movement of the second member 224 away from the rim 228. When the cam feature 275 of the locking plug 268 is not engaged with the cam features 296, 298 of the resilient elements 230, 232, the second member 224 may be moved toward or away from the rim 228. In the illustrated embodiment, the cam feature 275 of the locking plug 268 includes two prongs 300, 302 having convex outer surfaces, and the cam features 296, 298 of the resilient elements 230, 232 define concave recesses that receive the convex outer surfaces of the prongs 300, 302.

Referring to FIGS. 19-24, a method for performing a procedure on a spine of a patient is provided. The method includes positioning a post 226 of the first member 222 between two adjacent spinous processes 12a, 12b of the spine 14. The rim 228 may be positioned on a first side of the adjacent spinous processes 12a, 12b, and the second member 224 may be positioned on a second side of the adjacent spinous processes 12a, 12b opposite the first side. The second member 224 may be advanced, such as by sliding or rotational movement, along a length of the post 226 toward the second side of the adjacent spinous processes 12a, 12b. Third and fourth members 256, 262 may be mounted onto the post 226 between the rim 228 of the first member 222 and the second member 224 on opposite sides of the spinous processes 12a, 12b such that surface features 258, 266 of the members 256, 262 engage the spinous processes 12a, 12b as the second member 224 is advanced along the length of the post 226 towards the rim 228. As the second member 224 is advanced along the length of the post 226, the second member 224 may be automatically restricted from sliding along the length of the post 226 in a direction away from the adjacent spinous processes 12a, 12b, because of the interdigitation of corresponding latching features of the post 226 and the second member 224. During initial advancement of the second member 224 along the post 226, an inner surface 250 of the second member 224 may be ratcheted over ratchet threads or teeth 242, 244 of the resilient elements 230, 232 of the post 226 by the compressor 120, for example, to embed the surface features 258, 266 of the third and fourth members 256, 262 into the spinous processes 12a, 12b, thereby restricting movement of the spinous processes 12a, 12b relative to each other. After initial advancement, the second member 224 may be rotated relative to the post 226 by a tool, such as a nut driver or a wrench, to adjust the clamping force applied to the spinous processes 12a, 12b by the third and fourth members 256, 262.

Figure 21:
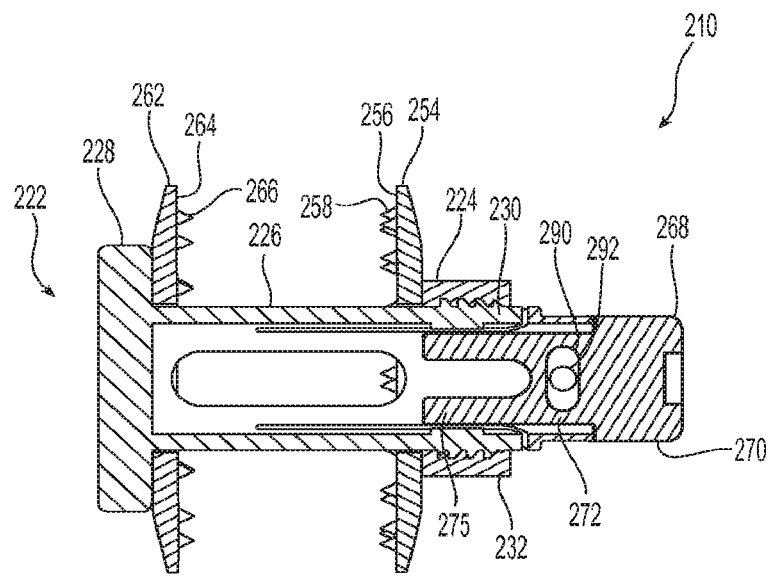
FIG. 21 is a longitudinal cross-section of the device of FIG. 11 taken along line 19-19 of FIG. 12 with a cross pin removed for description purposes in accordance with some embodiments of the present application.

To restrict the second member 224 from loosening during use, the second member 224 may define a groove 286 that receives a rib 288 of the third member 254. Additionally, or alternatively, a locking plug 268 may be disposed in the second end 226b of the post 226. The locking plug 268 may be moved relative to the post 226 to tighten a connection between second member 224 and the post 226, thereby substantially locking the axial position of the second member 224 relative to the post 226. In the embodiment illustrated in FIGS. 5-10, the locking plug 168 may include a conical or frustoconical surface 177 that contacts the inner surfaces 179 of the resilient elements 130, 132 to drive the resilient elements 130, 132 resiliently outwardly in a radial direction and tighten the connection between the resilient elements 130, 132 and the second member 124. In the embodiment illustrated in FIGS. 11-24, the locking plug 168 may be rotated relative to the post 126 to engage the cam feature 275 of the locking plug 268 with the cam features 296, 298 of the resilient elements 230, 232 of the post 226 and drive the resilient elements 230, 232 outwardly in a radial direction to tighten the connection between the resilient elements 230, 232 and the second member 224. The cam feature 275 of the locking plug 268 may be seated in the cam features 296, 298 of the resilient elements 230, 232 to maintain a tightened connection between the first and second members 222, 224. As shown in FIG. 21, the locking plug 268 may be inserted into the end 226b of the post 226 until the aperture 290 of the locking plug 268 is axially aligned with the apertures 292 of the post 226. Referring to FIG. 22, the cross pin 294 may be inserted through the apertures 290, 292 to axially constrain the locking plug 268 relative to the post 226. The aperture 290 of the locking plug 268 may be oversized relative to the cross pin 294 in a lateral direction to permit rotation of the locking plug 268 relative to the post 226. Rotation of the illustrated locking plug 268 relative to the post 226 selectively engages the cam feature 275 of the locking plug 268 with the cam features 296, 298 of the resilient element 230, 232 while the locking plug 268 remains in the same axial position relative to the post 226.

To remove the interspinous device 210 from between the two spinous processes 12a, 12b, the locking plug 268 may be rotated relative to the post 226 to disengage the cam features 275 and 296, 298. Then, the second member 224 may be unscrewed or unthreaded from the post 226 of the first member 222. The locking plug 268 may be removed from the end 226b of the post 226 before or after the second member 224 is removed from the post 226. In the embodiment illustrated in FIGS. 21 and 22, the locking plug 268 has an outer dimension that is smaller than an inner dimension of the second member 224, thereby permitting the second member to pass over the locking plug 224 without interference. To remove the locking plug 268 from the post 226, the cross pin 294 may be removed from the second end 226b of the post 226, and then the locking plug 268 may be moved in an axial direction away from the rim 228.

Figure 25:
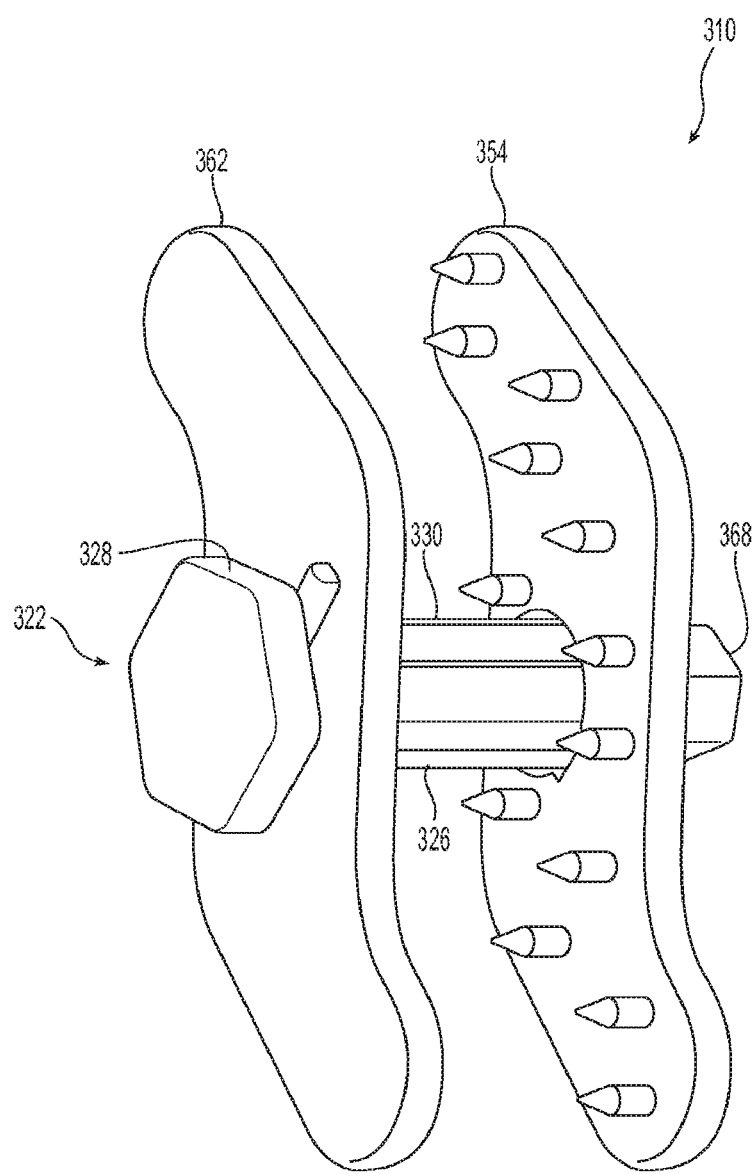
FIG. 25 is a perspective view of a device for placement between two adjacent spinous processes of a spinal column in accordance with some embodiments of the present application.

Referring to FIG. 25, another embodiment of a device 310 for placement between two adjacent spinous processes 12a, 12b of a spinal column 14 is depicted. The device 310 is similar to the devices 10, 110, 210 depicted in FIGS. 1-24. Accordingly, the preceding discussion related to the devices 10, 110, 210 is applicable to the device 310 shown in FIG. 25, except as noted below. The reference numerals used in FIG. 25 are incremented by one-hundred relative to the reference numerals used in FIGS. 11-24 to reflect similar parts.

Similar to the device 210 depicted in FIGS. 11-24, the device 310 of the illustrated embodiment includes a first member 322, a second member 324, a third member 354, a fourth member 362, and a locking plug 368. The first member 322 includes a post 326, a rim 328 extending around a periphery of the post 326, and one or more resilient elements 320 formed in the post 326. The third and fourth members 354, 362 may have lateral dimensions sufficient to span between and overlap the adjacent spinous processes 12a, 12b on opposite sides of the spinous processes 12a, 12b. As shown in FIG. 25, the third and fourth members 354, 362 have different shapes relative to the third and fourth members 254, 262 shown in FIGS. 11-24. The third and fourth members 354, 362 illustrated in FIG. 25 are elongate and include wing portions extending transversely away from each other and from the longitudinal axis of the post 226. In various alternative embodiments, the third and fourth members 354, 362 may be formed in various shapes, such as cylindrical, triangular, rectangular, or other polygonal and non-polygonal shapes suited for the particular spinal column.

The devices 10, 110, 210, 310 may be formed in various sizes to accommodate different sizes of patients. Various sizes may also accommodate different vertebrae within a given patient. An instrument set supplied to a surgeon may include several different sizes of devices 10, 110, 210, 310.

The devices 10, 110, 210, 310 may be made of any biocompatible materials. Example materials include, but are not limited to, metals, ceramics, polymers, composites, or other suitable types of biocompatible materials. In some embodiments, the devices 10, 110, 210, 310 are formed of titanium, titanium alloys, steel, steel alloys, or any combination thereof.

Although this invention has been disclosed in the context of certain preferred embodiments and examples, the present invention extends beyond the specifically disclosed embodiments to other alternative embodiments and/or uses of the invention and obvious modifications and equivalents thereof. Also, individual aspects of any embodiment can be claimed separately or in combination with aspects and features of that embodiment or any other embodiment. Thus, it is intended that the scope of the present invention herein disclosed should not be limited by the particular disclosed embodiments described above, but should be determined only by a fair reading of the claims that follow.

What is claimed is:

1. A device for placement between two adjacent spinous processes of a spinal column to treat a spinal condition, the device comprising:
   a first member, comprising:
      a post having a first end and a second end opposite the first end, the post including a body and a resilient element that is radially displaceable with respect to the body, the resilient element including an outwardly protruding latching feature at or near a free end of the resilient element that is disposed towards the second end of the post, wherein the resilient member has a base that depends from the post body, and wherein the free end is closer to the second end than the first end, and
      a rim disposed at or near the first end of the post and extending around a periphery of the post; and
   a second member mounted onto the post of the first member near the second end and movable along a length of the post to adjust a distance between the second member and the rim, the second member including a second latching feature which includes an inwardly protruding latching feature that cooperates with the outwardly protruding latching feature of the resilient element to restrict axial movement of the second member away from the rim.

2. A device as in claim 1, further comprising:
   a third member having an opening and receiving the post in the opening, the third member being disposed generally parallel to the rim including a first medial-facing surface that interfaces with the adjacent spinous processes, wherein the third member slides along the length of the post; and
   wherein the second latching feature limits movement of the third member away from the rim without impeding movement toward the rim.

3. A device as in claim 2, wherein the third member is positioned between the rim and the second member and the second member limits movement of the third member away from the rim in response to contact between the third member and the second member.

4. A device as in claim 3, wherein the third member includes a first set of one or more sharp protrusions on the medial-facing surface.

5. A device as in claim 3, further comprising a fourth member mounted on the post and disposed between the rim and the third member, the fourth member including a second medial-facing surface and a second set of sharp protrusions on the second medial-facing surface, wherein the first and second medial-facing surfaces face each other.

6. A device as in claim 1, wherein the second member further comprises an engagement feature protruding from a side of the second member facing away from the rim and configured for engagement with a tool.

7. A device as in claim 1, wherein the outwardly protruding latching feature comprises multiple teeth spaced apart from one another along a length of the resilient element, and wherein the second member is configured to ratchet onto the resilient element such that the inwardly protruding latching feature interdigitates with the teeth as the second member is advanced along the length of the resilient element.

8. A device as in claim 1, wherein the inwardly protruding latching feature is formed as an internal thread that is ratchetably and threadably engagable with the outwardly protruding latching feature of the resilient element.

9. A device as in claim 1, wherein the resilient element is defined at least partially by a U-shaped slit formed in the post.

10. A device as in claim 1, wherein the rim includes a first medial-facing surface and a first set of sharp protrusions on the first medial-facing surface.

11. A device as in claim 1, further comprising a locking plug inserted into a bore formed in the second end of the post to lock the second member onto the post.

12. A device as in claim 11, wherein the locking plug is engagable with an inner surface of the resilient element to tighten a connection between the first and second members.

13. A device as in claim 11, wherein the second member is removable from the post without removing the locking plug from the second end of the post.

14. A device as in claim 11, wherein the resilient element includes a first cam feature, and wherein the locking plug includes a second cam feature that is engagable with the first cam feature.

15. A device as in claim 14, wherein the locking plug is rotatable relative to the post to selectively engage the second cam feature with the first cam feature.

16. A device as in claim 15, further comprising a cross pin inserted through a first aperture formed in the post and a second aperture formed in the locking plug to substantially prevent axial movement of the locking plug relative to the post.

17. A device as in claim 16, wherein the second aperture is dimensioned to permit rotation of the locking plug relative to the post.

18. A device as in claim 1, wherein movement of the second member onto the length of the post causes the resilient member to resiliently displace towards a longitudinal axis of the post.

19. A device as in claim 12, wherein an engagement of the locking plug with the inner surface of the resilient element causes the free end of the resilient member to resiliently displace away from a longitudinal axis of the post.

20. A device for placement between two adjacent spinous processes of a spinal column to treat a spinal condition, the device comprising:
  a first member, comprising:
    a post having a first end and a second end opposite the first end, the post including a body and a resilient element that is radially displaceable with respect to the body, the resilient element including an outwardly protruding latching feature at or near a free end of the resilient element that is disposed towards the second end of the post, wherein the resilient element is defined at least partially by a U-shaped slit formed in the post,
    a rim disposed at or near the first end of the post and extending around a periphery of the post; and
  a second member mounted onto the post of the first member near the second end and movable along a length of the post to adjust a distance between the second member and the rim, the second member including a second latching feature which includes an inwardly protruding latching feature that cooperates with the outwardly protruding latching feature of the resilient element to restrict axial movement of the second member away from the rim.

21. A device for placement between two adjacent spinous processes of a spinal column to treat a spinal condition, the device comprising:
  a first member, comprising:
    a post having a first end and a second end opposite the first end, the post including a body and a resilient element that is radially displaceable with respect to the body, the resilient element including an outwardly protruding latching feature at or near a free end of the resilient element that is disposed towards the second end of the post,
    a rim disposed at or near the first end of the post and extending around a periphery of the post;
  a second member mounted onto the post of the first member near the second end and movable along a length of the post to adjust a distance between the second member and the rim, the second member including a second latching feature which includes an inwardly protruding latching feature that cooperates with the outwardly protruding latching feature of the resilient element to restrict axial movement of the second member away from the rim; and
  a locking plug inserted into a bore formed in the second end of the post to lock the second member onto the post.

* * * * *